(12) United States Patent
Avitable

(10) Patent No.: US 8,398,572 B2
(45) Date of Patent: Mar. 19, 2013

(54) BLADDER TUBE CONNECTION

(75) Inventor: Raymond C. Avitable, Framingham, MA (US)

(73) Assignee: Covidien LP, Mansfield, MA (US)

( * ) Notice: Subject to any disclaimer, the term of this patent is extended or adjusted under 35 U.S.C. 154(b) by 65 days.

(21) Appl. No.: 12/886,864

(22) Filed: Sep. 21, 2010

(65) Prior Publication Data

US 2012/0071801 A1    Mar. 22, 2012

(51) Int. Cl.
*A61H 1/00* (2006.01)
*A61F 5/37* (2006.01)

(52) U.S. Cl. ............ 601/151; 601/5; 601/148; 601/152; 128/878; 128/882; 602/13; 606/192

(58) Field of Classification Search .............. 601/5, 148, 601/151, 152; 128/878, 882; 602/13; 606/192
See application file for complete search history.

(56) References Cited

U.S. PATENT DOCUMENTS

| | | | |
|---|---|---|---|
| 2,422,525 A | 6/1947 | Brown et al. |
| 2,764,862 A | 10/1956 | Rado |
| 2,816,596 A | 12/1957 | Welch, Jr. |
| 2,941,575 A | 6/1960 | Malmberg et al. |
| 3,454,442 A | 7/1969 | Heller, Jr. |
| 3,574,031 A | 4/1971 | Heller, Jr. et al. |
| 3,583,458 A | 6/1971 | Costa |
| 3,783,217 A | 1/1974 | Brown |
| 3,945,867 A | 3/1976 | Heller, Jr. et al. |
| 4,023,607 A | 5/1977 | Jensen et al. |
| 4,091,804 A | 5/1978 | Hasty |
| 4,126,167 A | 11/1978 | Smith et al. |
| 4,352,669 A | 10/1982 | Norton |
| 4,384,186 A | 5/1983 | Burt |
| 4,390,832 A | 6/1983 | Taylor |
| 4,417,122 A | 11/1983 | Thorne |
| 4,417,753 A | 11/1983 | Bacehowski et al. |
| 4,425,177 A | 1/1984 | Shinno |
| 4,453,538 A | 6/1984 | Whitney |

(Continued)

FOREIGN PATENT DOCUMENTS

DE    10 2006 004 611 A1    8/2007
EP         0 200 483 A2    11/1986

(Continued)

OTHER PUBLICATIONS

Yousefpour, "Fusion Bonding/Welding of Thermoplastic Composites", Journal of Thermoplastic Composite Materials, vol. 17, No. 4, Jan. 1, 2004, pp. 303-341.

*Primary Examiner* — Clinton T Ostrup
(74) *Attorney, Agent, or Firm* — John Paul Mello, Esq.

(57) ABSTRACT

A compression device for applying compression treatment to a patient's body. The device includes an inflatable bladder having an inner layer, an outer layer opposite the inner layer, the inner layer and the outer layer are joined to form a hollow interior adapted for periodically receiving fluid to inflate the bladder, the joined layers are joined by a seam having a sealed upstream end, an open downstream end, and sealed lateral sides. The bladder includes an opening positioned between the lateral sides and extending through the inner layer and/or the outer layer of the bladder. The device includes the tube extending toward the open downstream end of the seam and through the opening. The device includes a seal extending between the lateral sides of the seam and across the tube preventing fluid leakage between the tube and the opening in the bladder when the bladder is inflated.

18 Claims, 4 Drawing Sheets

U.S. PATENT DOCUMENTS

| | | | |
|---|---|---|---|
| 4,465,487 A | 8/1984 | Nakamura et al. | |
| 4,484,904 A | 11/1984 | Fowler | |
| 4,496,095 A | 1/1985 | Renshaw et al. | |
| 4,549,684 A | 10/1985 | Telly et al. | |
| 4,600,613 A | 7/1986 | Yoshida | |
| 4,650,452 A | 3/1987 | Jensen | |
| 4,809,684 A | 3/1989 | Gardner et al. | |
| 4,836,691 A | 6/1989 | Suzuki et al. | |
| 4,876,788 A | 10/1989 | Steer et al. | |
| 4,892,604 A | 1/1990 | Measells et al. | |
| 4,950,347 A | 8/1990 | Futagawa | |
| 4,979,953 A | 12/1990 | Spence | |
| 5,047,605 A | 9/1991 | Ogden | |
| 5,278,382 A | 1/1994 | Rische et al. | |
| 5,324,233 A | 6/1994 | Owensby et al. | |
| 5,336,123 A * | 8/1994 | Laske et al. | 446/224 |
| 5,349,166 A | 9/1994 | Taylor | |
| 5,354,260 A | 10/1994 | Cook | |
| 5,427,645 A | 6/1995 | Lovin | |
| 5,437,595 A | 8/1995 | Smith | |
| 5,507,904 A | 4/1996 | Fisher et al. | |
| 5,591,337 A | 1/1997 | Lynn et al. | |
| 5,678,732 A | 10/1997 | Gianpaolo | |
| 5,769,801 A | 6/1998 | Tumey et al. | |
| 5,803,888 A | 9/1998 | Severs et al. | |
| 5,840,049 A | 11/1998 | Tumey et al. | |
| 5,976,300 A | 11/1999 | Buchanan | |
| 5,989,204 A | 11/1999 | Lina | |
| 6,001,119 A | 12/1999 | Hampson et al. | |
| 6,011,235 A | 1/2000 | Mukai et al. | |
| 6,036,718 A | 3/2000 | Ledford et al. | |
| 6,127,009 A | 10/2000 | Strassmann | |
| 6,259,059 B1 | 7/2001 | Hsu | |
| 6,486,456 B1 | 11/2002 | Moro et al. | |
| 6,601,710 B2 | 8/2003 | Calhoun et al. | |
| 6,652,942 B2 | 11/2003 | Ling et al. | |
| 6,828,536 B1 | 12/2004 | Grimes et al. | |
| 7,012,232 B1 | 3/2006 | Gruenspecht et al. | |
| 7,041,936 B2 | 5/2006 | Oberzaucher et al. | |
| 7,237,290 B2 | 7/2007 | Bichler | |
| 7,353,946 B2 | 4/2008 | Cervantes | |
| 7,399,375 B2 | 7/2008 | Leiser et al. | |
| 7,586,071 B2 | 9/2009 | Gruenspecht et al. | |
| 8,151,851 B2 | 4/2012 | Vess | |
| 2004/0054306 A1 | 3/2004 | Roth et al. | |
| 2004/0133135 A1 | 7/2004 | Diana | |
| 2004/0199090 A1 | 10/2004 | Sanders et al. | |
| 2007/0038167 A1 | 2/2007 | Tabron et al. | |
| 2007/0045240 A1 | 3/2007 | Smith et al. | |
| 2007/0135835 A1 | 6/2007 | McEwen et al. | |
| 2008/0149609 A1 | 6/2008 | Vess | |
| 2008/0249447 A1 * | 10/2008 | Brown et al. | 602/13 |
| 2008/0269658 A1 | 10/2008 | Vinton et al. | |
| 2009/0069731 A1 | 3/2009 | Parish et al. | |
| 2010/0004575 A1 * | 1/2010 | Vess | 601/152 |
| 2010/0320193 A1 | 12/2010 | Vess | |

FOREIGN PATENT DOCUMENTS

| | | |
|---|---|---|
| EP | 0 221 636 A1 | 5/1987 |
| EP | 0 339 494 A2 | 11/1989 |
| EP | 0 344 949 A2 | 12/1989 |
| EP | 1 795 168 B1 | 6/2007 |
| EP | 1 935 616 A2 | 6/2008 |
| EP | 2140850 A1 * | 1/2010 |
| EP | 2 168 555 A1 | 3/2010 |
| FR | 914433 | 10/1946 |
| GB | 2 193 485 A | 2/1988 |
| JP | 08-038580 | 2/1996 |
| JP | 8025227 B | 3/1996 |
| WO | 98/09872 | 3/1998 |

* cited by examiner

BLADDER TUBE CONNECTION

BACKGROUND

The present invention is directed generally to a compression device for applying compression therapy to a body part of a wearer, more particularly a compression sleeve.

A major concern for immobile patients and like persons are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popiteal and tibial return deoxygenated blood to the heart. For example, when blood circulation in these veins is retarded due to illness, injury or inactivity, there is a tendency for blood to accumulate or pool. A static pool of blood may lead to the formation of a blood clot. A major risk associated with this condition is interference with cardiovascular circulation. Most seriously, a fragment of the blood clot can break loose and migrate. A pulmonary emboli can form from the fragment potentially blocking a main pulmonary artery, which may be life threatening. The current invention can also be applied to the treatment of lymphedema.

The conditions and resulting risks associated with patient immobility may be controlled or alleviated by applying intermittent pressure to a patient's limb, such as, for example, a leg to assist in blood circulation. For example, sequential compression devices have been used, such as the device disclosed in U.S. Pat. No. 4,091,804 (Hasty). Sequential compression devices are typically constructed of two sheets of material secured together at the seams to define one or more fluid impervious bladders. Tubes extending from the bladders are connected to a fluid source for applying sequential pressure around a patient's body parts for improving blood return to the heart. The tubes are connected to the bladders by molded port connectors that are welded to the bladders. The connectors add additional components to the device, increasing cost. The connectors are generally stiff, causing discomfort when pressed against the skin of the wearer. Further, the connectors must be carefully positioned and oriented during design and final assembly.

SUMMARY

The present invention relates to a compression device for applying compression treatment to a part of a patient's body. The device includes an inflatable bladder having an inner layer positioned in use to face the patient's body, an outer layer opposite the inner layer positioned in use to face away from the patient's body, the inner layer and the outer layer are joined to form a hollow interior adapted for periodically receiving fluid to inflate the bladder, the joined inner layer and outer layer are further joined by a seam having a sealed upstream end, an open downstream end, and sealed lateral sides extending between the upstream end and the downstream end, the bladder including an opening positioned between the lateral sides of the seam and extending through at least one of the inner layer and the outer layer of the bladder. The device also includes the tube extending toward the open downstream end of the seam and through the opening positioned between the lateral sides of the seam in the bladder, the tube being adapted for connection to a fluid source for deliver fluid from the source to the hollow interior to inflate the bladder. The device also includes a seal extending between the lateral sides of the seam and across the tube preventing fluid leakage between the tube and the opening in the bladder when the bladder is inflated.

The invention further relates to a compression device for applying compression treatment to a part of a patient's body. The sleeve includes a sleeve sized for fastening around the part of the patient's body. The sleeve also includes an inflatable bladder mounted on the sleeve having an inner layer positioned in use to face the patient's body, an outer layer opposite the inner layer positioned in use to face away from the patient's body, the inner layer and the outer layer being joined to form a hollow interior adapted for periodically receiving fluid to inflate the bladder, the joined inner layer and outer layer being further joined by a seam having a sealed upstream end, an open downstream end, and sealed lateral sides extending between the upstream end and the downstream end, the bladder including an opening positioned between the lateral sides of the seam and extending through at least one of the inner layer and the outer layer of the bladder. The sleeve also includes the tube extending toward the open downstream end of the seam and through the opening positioned between the lateral sides of the seam in the bladder, the tube being adapted for connection to a fluid source for deliver fluid from the source to the hollow interior to inflate the bladder. The sleeve also includes a seal extending between the lateral sides of the seam preventing fluid leakage between the tube and the opening in the bladder when the bladder is inflated.

BRIEF DESCRIPTION OF THE DRAWINGS

Corresponding reference characters indicate corresponding parts throughout the drawings.

DETAILED DESCRIPTION OF THE DRAWINGS

Figure 1:
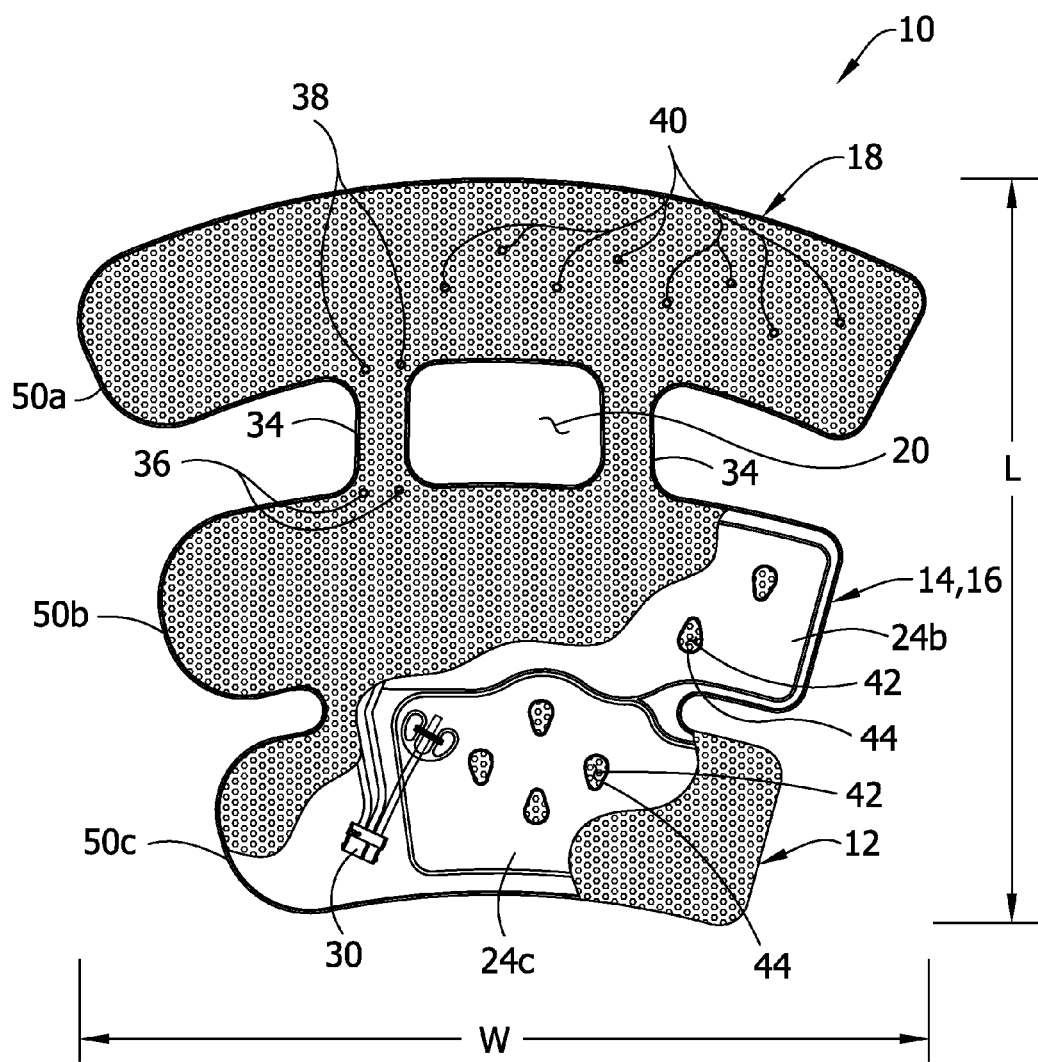
FIG. 1 is a front elevation of a compression sleeve with an outer cover and intermediate layers of the sleeve partially removed to show underlying layers.

Referring now to the drawings and in particular to FIG. 1, one embodiment of a compression device for applying sequential compression therapy to a limb of a wearer is generally indicated by the reference number 10. The illustrated compression sleeve is sized and shaped for wrapping around a leg of the wearer, but could be configured for application to other parts of the wearer's body. More specifically, the sleeve 10 has a width W (FIG. 1) for being wrapped around a full circumference of the leg and a length L (FIG. 1) for running from the ankle to a thigh of the leg. This type of sleeve is generally referred to in the art as a thigh-length sleeve. It will be understood that a compression sleeve may have different sizes, such as a knee-length sleeve that extends from the ankle up the calf of the leg to the knee. It should be understood that other types of compression devices for wrapped around other limbs of the wearer's body are within the scope of this invention, such as a wrap around a patient's chest in the treatment of breast cancer.

Referring to FIG. 1, in the illustrated embodiment of the present invention the compression sleeve 10 comprises four layers secured together, but the scope of the present invention is not limited to four layers. More specifically, the compression sleeve comprises an inner liner or sheet, generally indicated at 12, on which a first intermediate layer (or inner bladder layer), generally indicated at 14, is overlaid. A second intermediate layer (or outer bladder layer), generally indicated at 16, overlies the first intermediate layer 14 and is secured thereto. An outer cover or sheet, generally indicated at 18, overlies and is secured to the second intermediate layer 16. In use, the inner liner 12 is disposed closest to the limb of the wearer and is in contact with the limb of the wearer, and the outer cover 18 is farthest from the limb of the wearer. A knee opening 20 is formed through the sleeve 10 that is generally aligned with the back of the knee when the sleeve is applied to the leg. The layers generally have the same geometric shape and are superposed on each other so edges of the layers generally coincide. It is contemplated that one or more of the layers 12, 14, 16, or 18 may not be superposed on a corresponding layer, but slightly offset to accommodate a particular feature of a patient's limb. Moreover, the number of sheets or thickness making up each layer 12, 14, 16, or 18 of the compression sleeve 10 may be other than described. The thickness of the layers may vary to change strength or to cause more expansion in one direction, such as toward the limb, during inflation.

Figure 2:
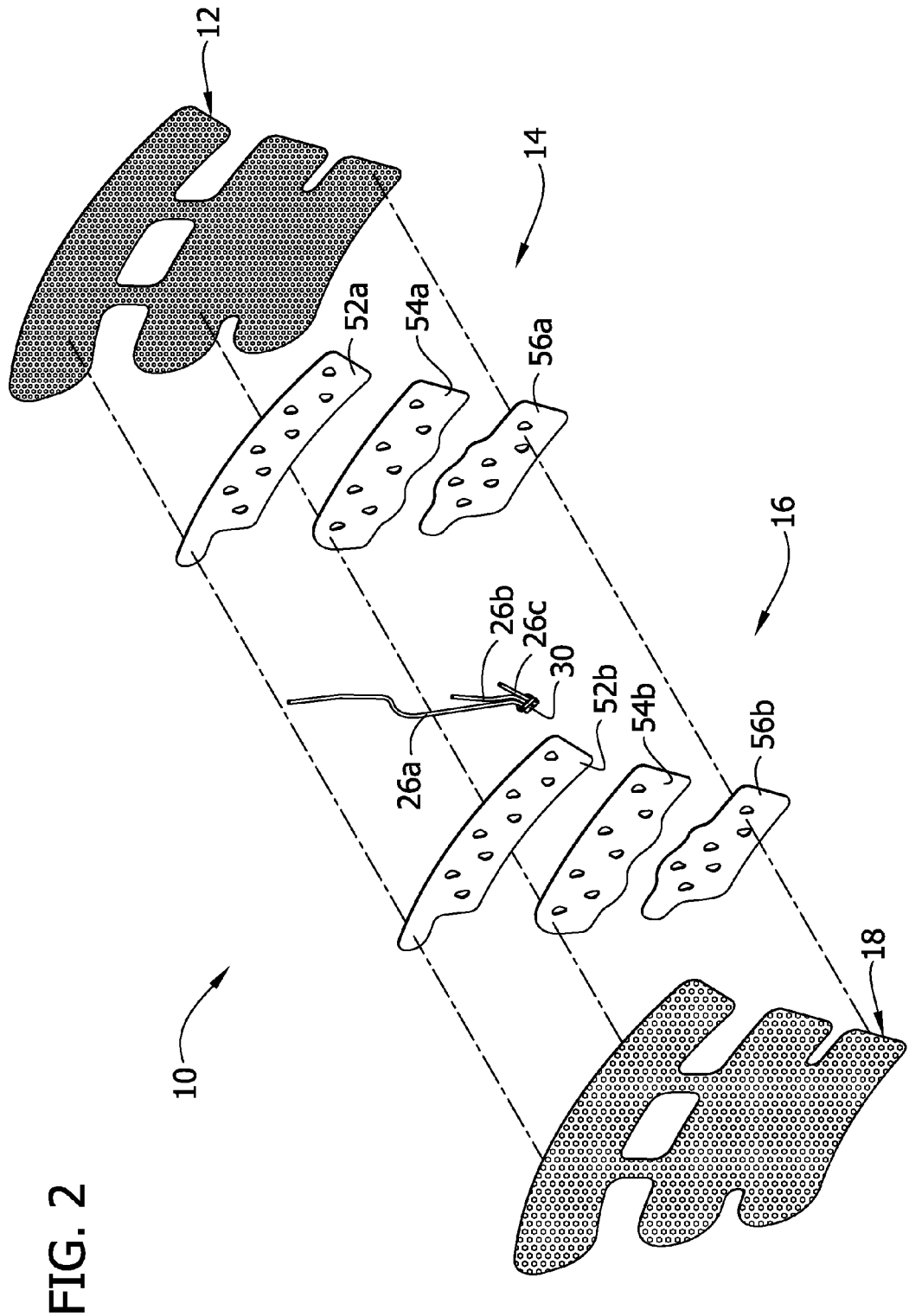
FIG. 2 is a separated perspective of the sleeve.

Referring to FIG. 2, the inner and second intermediate layers 14, 16, respectively, each include a single sheet of elastic material. For example, the sheets 14 and 16 are made of a pliable PVC material as the bladder material. Layers 12 and 18 are made of a polyester material. The second intermediate layer 16 is secured to the first intermediate layer 14 via three separate bladder seam lines 22a, 22b, 22c defining a proximal bladder 24a, an intermediate bladder 24b and a distal bladder 24c, respectively, that are spaced longitudinally along the sleeve 10. The number of bladders may be other than three without departing from the scope of the present invention. As used herein, the terms "proximal", "distal", and "intermediate" represent relative locations of components and parts of the compression sleeve when the sleeve is secured to the wearer's limb. As such, a "proximal" component is disposed closest to a point of attachment of the wearer's limb to the wearer's torso, a "distal" component is disposed farthest from the point of attachment, and an "intermediate" component is disposed generally anywhere between the proximal and distal components.

For reasons discussed below, the proximal bladder 24a defines a proximal, lateral extension 25 near an upper edge margin of the sleeve 10. The bladders 24a, 24b, 24c are circumferential bladders meaning that they are sized and shaped to be wrapped around substantially the entire circumference of the wearer's limb or very nearly the entire circumference of the limb. For example, in one embodiment the bladders 24a, 24b, 24c each extend around at least 90% of a median circumference of a leg. It should be understood that the construction described herein can be adopted by sleeves with a partial bladder construction without departing from the scope of the present invention.

The intermediate layers 14, 16 may be secured together by radiofrequency welding, adhesive, or other chemical and/or mechanical processes. Further, the intermediate layers 14, 16 may be secured together at other locations, such as around their peripheries and at bladder seam lines 22a, 22b, 22c to further define the shape of the inflatable bladders 24a, 24b, 24c. For purposes discussed below, the first intermediate layer 14 is secured to the inner liner 12 along a seam (not shown) running along the outer periphery of the first intermediate layer 14 so central regions of the bladders 24a, 24b, 24c are not secured to the inner liner 12, permitting the bladders move relative to the inner liner. The second intermediate layer 16 may also be secured to the inner liner 12 along the same seam line. The first intermediate layer 14 may be secured to the inner liner 12 by RF welding or adhesive or in other ways. This structure improves comfort as described below.

Referring to FIG. 2, each inflatable bladder 24a, 24b, 24c receives fluid from a source of compressed fluid (not shown) via a dedicated proximal bladder tube 26a, intermediate bladder tube 26b, and distal bladder tube 26c, respectively, (FIG. 2). Each tube 26a, 26b, 26c is secured to the respective bladder 24a, 24b, 24c as will be explained in greater detail below. The upstream ends of the tubes 26a, 26b, 26c are grouped together and joined by a connector 30 adapted to fluidly connect the tubes to the source of compressed fluid. The source of compressed fluid may be an air compressor under the control of a microprocessor that sequentially pressurizes the bladders as is generally known in the art. An exemplary air compressor is described in U.S. Pat. No. 5,876,359 (Bock) which is incorporated herein by reference. The bladders 24a, 24b, 24c may be configured to contain air pressurized to a pressure in a range from about 10 mm Hg (about 1333 Pa) to about 45 mm Hg (about 6000 Pa). The bladders should be capable of being repeatedly pressurized without failure. Materials suitable for the sheets include, but are not limited to, flexible PVC material that will not stretch substantially. In another embodiment, the intermediate layers may form a chamber for receiving an inflatable bladder that is formed separate from the chamber. In this embodiment, the layers may not be capable of containing pressurized air as along as the inflatable bladders are so capable. It will be noted that the bladders 24a, 24b, 24c can have openings 42 extending completely through the bladders, as described in the embodiments of the present invention.

Figure 3:
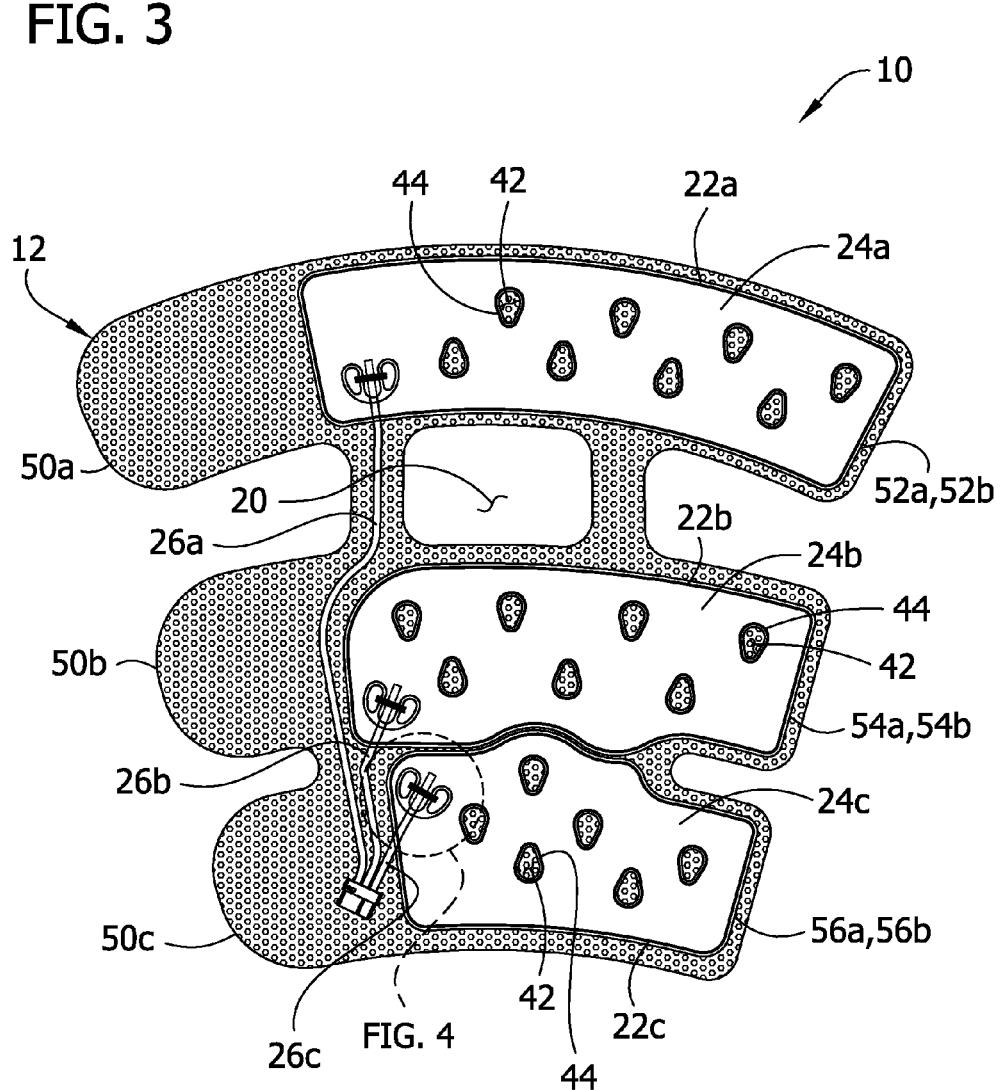
FIG. 3 is a front elevation of the sleeve with the outer cover removed.

Referring particularly to FIG. 1, the sleeve 10 defines a connecting section including a pair of bridge members 34 on opposite sides of the knee opening 20 that extend between and connect a proximal portion of the sleeve including the proximal bladder 24a to the remainder of the sleeve. As shown in FIG. 3, the proximal tube 26a generally lies along an axis of the bridge member 34 to provide structural, lengthwise support to the sleeve 10. As further illustrated in FIG. 1, the proximal tube 26a extends between spaced distal spot welds 36 disposed adjacent a distal end of the bridge member 34 and between spaced proximal spot welds 38 disposed adjacent a proximal end of the bridge member. The spot welds secure the tube 26a to the bridge member 34 so the proximal bladder tube 26a constitutes a rigid structural component for maintaining the spacing between the proximal bladder 24a and the intermediate bladder 24b and maintaining the longitudinally structural integrity of the connecting section. In other words, the sleeve 10 is made more rigid to prevent collapsing or sliding down the wearer's leg.

As shown in FIG. 3, the proximal bladder 24a is secured to the inner liner 12 and the outer cover 18 at spot welds 40 (FIG. 1) adjacent bladder openings 42 defined by seamlines 44 positioned inside an outer perimeter of the bladder. The spot welds 40 maintain the outer cover 18 and the inner liner 12 in proper position with respect to the bladders 24a, 24b, 24c. In other words, the spot welds 40 prevent the bladders 24a, 24b, 24c from substantially shifting relative to the inner liner 12 and the outer cover 18 while providing the sleeve 10 with substantial flexibility. Too much movement of the inner liner 12 and the outer cover 18 with respect to the bladders 24a, 24b, 24c may reduce the fit of the sleeve, thereby leading to reduced efficacy of the compression therapy. The proximal bladder 24a is not secured to the inner liner 12 and outer cover 18 other than at the spot welds 40 to maintain flexibility of the sleeve so the patient's leg mobility is not compromised. The inner liner 12 may be joined to layer 16 at the spot welds 36, 38, 40 or the inner liner 12 may be joined at the seamlines 44 defining the openings 42. Away from the openings 42 and spot welds 36, 38, 40, the inner liner 12 is not joined to the bladder material forming the bladders.

In one embodiment, the bladders 24a, 24b, 24c are constructed to expand more toward the wearer than away from the wearer, thereby applying a greater compressive force on the wearer's limb. In one example, the first intermediate layer 14 (i.e., the layer closest to the inner liner 12) is thinner than that of the second intermediate layer 16. With both layers 14, 16 being of the same material (i.e., elastic PVC material) the first intermediate sheet will have a lower modulus of elasticity. Thus, when air is introduced into the bladders 24a, 24b, 24c, the bladders will expand more toward the inner liner 12 and the wearer than away from the wearer. It is understood that other ways, besides a difference in thickness between the intermediate layers 14, 16, of constructing the bladders 24a, 24b, 24c so that they expand more toward the wearer than away from the wearer is within the scope of the invention.

Referring to FIG. 2, the inner liner 12 is constructed of a material that is capable of wicking moisture away from a patient's limb. The inner liner 12, through capillary action, absorbs moisture trapped near the leg or limb of the wearer, carries the moisture away from the surface of the limb, and transports the moisture from locations on the limb at the inner liner where the moisture is abundant to areas at the openings 42 where the moisture is less abundant for evaporation to the ambient environment. The openings 42 may be of various sizes, shapes and locations within the bladder area providing the compression. An opening 42 exposes the wicking layer to the ambient or surrounding air as opposed to the portion of the wicking layer beneath the bladder material. The portions of the inner liner 12 aligned registration with the openings 42 may be referred to as "exposed portions". Other ways of exposing the wicking material are within the scope of this invention, such as slits or extending the wicking material outside the perimeter of the bladder material. The openings 42 are preferably designed to maintain blood velocity, while maximizing evaporation of moisture. Suitable wicking materials may comprise polyester or polypropylene. Microfibers may be used. Suitable microfiber materials include, but are not limited to, COOLDRY® material, model number CD9604, sold by Quanzhou Fulian Warp Knitting Industrial Co., Ltd., Quanzhou City, Fujian Province, China and COOLMAX® material, sold by E. I. du Pont de Nemours and Company, Wilmington, Del.

The construction of wicking layer, openings, bladder, and outer layer is discussed. The openings must be sized and shaped to maintain the blood flow efficacy of a compression sleeve like model 9529 and to provide improved evaporation of moisture for increasing patient compliance. Referring to FIGS. 1 and 3, the sleeve 10 is constructed so that portions of the intermediate layers 14, 16 do not overlie the inner liner 12 so that moisture wicked by the inner liner 12 travels to open portions of the inner liner 12 and evaporates to the atmosphere. In this illustrated embodiment, each inflatable bladder 24a, 24b, 24c includes openings 42 that extend through the first and second intermediate layers 14, 16, respectively, to the inner liner 12. One way to form such an opening is to seal the intermediate layers 14, 16 together within the periphery of the respective bladder 24a, 24b, 24c at the seamlines 44. The portions of the intermediate layers 14, 16 within a periphery of the each seamline 44 can be removed, such as by cutting, thereby forming the openings 42. Once an opening size and pattern is determined, a metal die is formed to cut the openings in the PVC bladder material for the opposing sheets.

For one preferred embodiment, the opening shape is generally shaped like a teardrop. Each opening 42 is tapered from a first round end portion toward a second, smaller round end portion. The openings 42 may be of other shapes, such as circles, ovals, and slits, without departing from the scope of the invention. The opening shapes may be inter-mixed at the bladder without departing from the scope of the invention.

Referring to FIGS. 1 and 2, the outer cover 18 of the compression sleeve 10 is constructed of a single sheet of material. The outer cover 18 is breathable and has a multiplicity of openings or perforations so that it has a mesh construction to provide even more breathability. A suitable material for the outer cover 18 may be a polyester mesh. The rate of evaporation from the openings is improved by treating the fibers of the mesh material with a hydrophilic material. The mesh material will absorb the wicked fluid more readily. These hydrophilic fibers lower the surface tension of the mesh material to allow bodily fluids to more easily absorb into the fibers and spread therethrough for a more efficient evaporation of the wicked fluid. Absorbing fluid more readily will allow the fluid to move to the open areas 42 more quickly for evaporation. The capillary effect is made more efficient as the absorbed fluid at the openings is moved more quickly through the mesh outer cover 18. Referring to FIG. 1, the outer cover 18 is secured to the second intermediate layer 16 along the seamline 48 running adjacent the outer periphery of the second intermediate layer so the bladders 24a, 24b, 24c are unattached to the cover. The second intermediate layer 16 may be secured to the inner liner 12 by RF welding or adhesive or in other ways.

The entirety of an outer surface of the outer cover 18 acts as a fastening component of a fastening system for securing the sleeve 10 to the limb of the wearer. In one particular embodiment, the outer cover 18 has an outer surface comprising loops that act as a loop component of a hook-and-loop fastening system. The loops may be formed as part of the material of the outer cover 18 or otherwise disposed on the surface of the outer cover. A suitable material with such construction is a polyester mesh loop 2103 sold by Quanzhou Fulian Warp Knitting Industrial Co., Ltd. of Quanzhou City, China. Conventional hook components (not shown) are attached to an inner surface of the inner liner 12 at the proximal, intermediate and distal flaps 50a, 50b, 50c, respectively. The loops of the outer cover 18 allow the hook components to be secured anywhere along the outer surface of the outer cover when the sleeve 10 is wrapped circumferentially around the limb of the wearer. This allows for sleeve 10 to be of a substantially one-size-fits-all configuration with respect to the circumferences of different wearers' limbs. Moreover, the outer cover 18 having the loops allows the practitioner to quickly and confidently secure the sleeve 10 to the wearer's limb without needing to align the fastening components.

It is contemplated that the outer cover 18 may be capable of wicking fluid in addition to being breathable. For example, the outer cover 18 may be constructed of the same material as the inner liner 12 (e.g., COOLDRY® material). In this way, the moisture wicked by the inner liner 12 may be wicked by the outer cover 18 through the openings 42 in the bladders 24a, 24b, 24c. The moisture will then spread out evenly across the outer cover 18 and is able to evaporate more readily than if the outer cover was not formed of a wicking material because a greater surface area of the outer cover, as opposed to the inner liner 12, is exposed to air. Alternatively, the cover can have a wicking material laced in or on top of outer layer.

As illustrated in FIG. 3, in one embodiment each of the intermediate layers 14, 16 comprises three separate sheets 52a, 54a, 56a and 52b, 54b, 56b, respectively. Corresponding intermediate sheets 52a, 52b and 54a, 54b and 56a, 56b are secured together to form the three separate bladders 24a, 24b, 24c. It is also contemplated that adjacent bladders 24a, 24b, 24c may be connected to each other by elastically stretchable material other than the inner liner 12.

As is known in the art, the bladders 24a, 24b, 24c are pressurized to different pressures. For example, the distal bladder 24c is pressurized to a higher pressure than the intermediate bladder 24b. The wavy portion of the seam lines 22c, 22b creates a transition section defined by the wavy portion having a pressure that is between the high pressure of the distal bladder 24c and the lower pressure of the intermediate bladder 24b. The wavy transition section, in effect, avoids a region of essentially zero pressure and helps prevent pooling of blood between the adjacent bladders 24b, 24c. Industry studies performed by Nicolaides, Olson and Best all describe the importance of preventing the pooling of blood that can lead to venous stasis—a condition having a high occurrence of leading to a pulmonary embolism.

Figure 4:
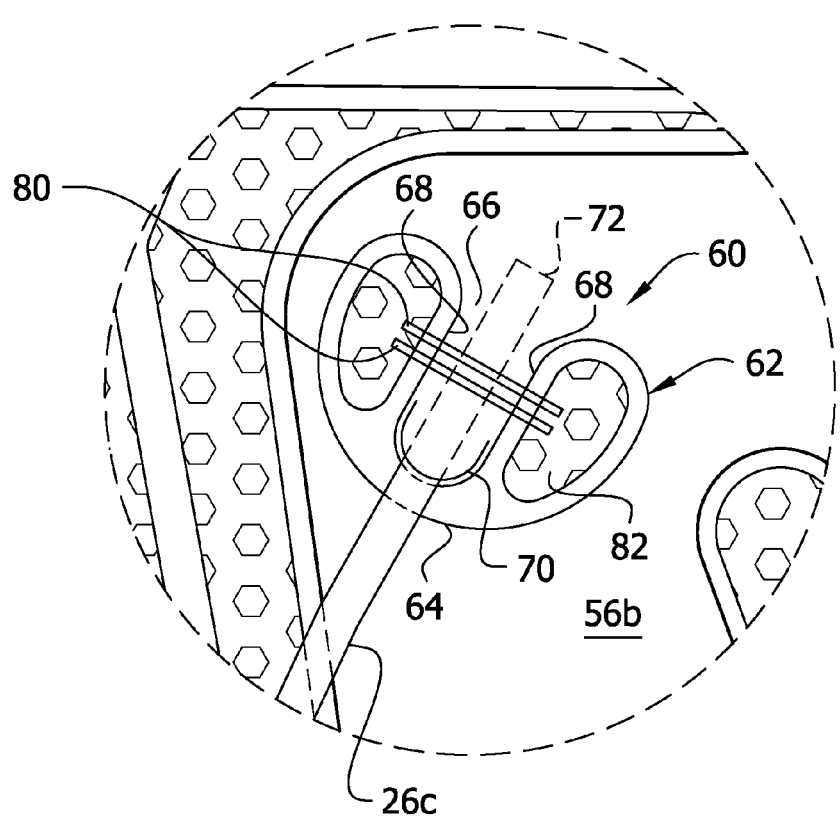
FIG. 4 is a detail of an area indicated in FIG. 3.

As shown in FIG. 4, the tube 26c are connected to the bladder 24c using a connection system, generally designated by 60. The system 60 includes a seam, generally designated by 62, joining the first intermediate layer 14, 56a to the second intermediate layer 16, 56b. The seam 62 has a sealed upstream end 64, an open downstream end 66, and sealed lateral sides 68 extending between the upstream end and the downstream end. The system 60 also includes an opening 70 positioned between the lateral sides 68 of the seam 60. In one embodiment, the opening 70 extends through the second intermediate layer 16, 56b (i.e., the outer layer of the bladder 24c). Although the seam 62 may be formed using other methods, in one embodiment, the seam is formed using a welding method similar to that described above with respect to the seamlines 44 defining the bladder openings 42. In one embodiment, the seam 62 is formed so it has a rounded section at its upstream end 64 a teardrop shape section at its lateral sides 68. Further, the inboard margins of the lateral sides 68 comprise straight sections as shown in FIG. 4. Although the opening 70 may have other shapes without departing from the scope of the present invention, in one embodiment the opening has a U-shaped portion as illustrated. The tube 26c is inserted through the opening 70 as shown so that the portion of the tube inside the bladder 24c extends from the opening toward the open end 66 of the seam 62 to an open end 72 of the tube. The system 60 also includes a seal 80, which in one embodiment is formed by a pair of parallel welds, extending between the lateral sides 68 of the seam 62 and across the tube 26c preventing fluid leakage between the tube and the opening 70 in the bladder 24c when the bladder is inflated. Although the seal 80 is formed by a pair of parallel welds in the illustrated embodiment, those skilled in the art will appreciate that the seal may be formed by one weld or multiple welds without departing from the scope of the present invention. The seal 80 may be formed by any suitable means that seals together the layers 56a, 56b forming the bladder 24c with each other and with the tube 26c without sealing a passage inside the tube 26c closed. One such seal is formed by RF welding. Although the system 60 is described with respect to the distal bladder 24c, it will be understood that the system is substantially similar for each of the other tube-to-bladder connections.

In one embodiment, the teardrop shape sections of the seam 62 include air passages 82 similar to the openings 42 formed by the seamlines 44 to allow air to pass through the bladder between the inner liner 12 and the cover 18.

The compression device described above is conventional in many respects and will not be described in further detail. Further information about the preferred embodiment may be found in U.S. patent application Ser. No. 11/733,095 (Brown) filed Apr. 9, 2007, which is incorporated by reference.

As will be appreciated by those skilled in the art, the compression device 10 of the present invention provides several advantages over many of those found in the prior art. For example, by eliminating separate molded connectors for joining the bladders 24a, 24b, 24c to the tubes 26a, 26b, 26c, three elements of the device 10 are eliminated. By eliminating elements, cost and complexity are reduced. Further, the connections of the present invention provide relatively soft connections. When the connectors press against the wearer, they are less likely to cause discomfort.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A compression device for applying compression treatment to a part of a patient's body, the device comprising:
    an inflatable bladder having an inner layer positioned in use to face the patient's body, an outer layer opposite the inner layer positioned in use to face away from the patient's body, the inner layer and the outer layer being joined to form a hollow interior adapted for periodically receiving fluid to inflate the bladder, the joined inner layer and outer layer being further joined by a seam having a sealed upstream end, an open downstream end, and sealed lateral sides extending between the upstream end and the downstream end, the bladder including an opening positioned between the lateral sides of the seam and extending through at least one of the inner layer and the outer layer of the bladder;
    the tube extending toward the open downstream end of the seam and through the opening positioned between the lateral sides of the seam in the bladder, the tube being adapted for connection to a fluid source for delivering fluid from the source to the hollow interior to inflate the bladder; and
    a seal extending between the lateral sides of the seam and across the tube preventing fluid leakage between the tube and the opening in the bladder when the bladder is inflated.

2. A compression device as set forth in claim 1 wherein the upstream end of the seam comprises a rounded section.

3. A compression device as set forth in claim 2 wherein the lateral sides of the seam comprise a straight section.

4. A compression device as set forth in claim 2 wherein the lateral sides of the seam comprise a teardrop shape section.

5. A compression device as set forth in claim 4 wherein the teardrop shape section of the seam includes a central air passage allowing air to pass through the bladder between the inner layer and the outer layer.

6. A compression device as set forth in claim 1 wherein the opening in the bladder comprises a generally U-shaped portion.

7. A compression device as set forth in claim 1 wherein the seal comprises a weld extending between the lateral sides of the seam and across the tube.

8. A compression device as set forth in claim 1 wherein the opening in the bladder extends through the outer layer of the bladder.

9. A compression device for applying compression treatment to a part of a patient's body, the sleeve comprising:
- a sleeve sized for fastening around the part of the patient's body;
- an inflatable bladder mounted on the sleeve having an inner layer positioned in use to face the patient's body, an outer layer opposite the inner layer positioned in use to face away from the patient's body, the inner layer and the outer layer being joined to form a hollow interior adapted for periodically receiving fluid to inflate the bladder, the joined inner layer and outer layer being further joined by a seam having a sealed upstream end, an open downstream end, and sealed lateral sides extending between the upstream end and the downstream end, the bladder including an opening positioned between the lateral sides of the seam and extending through at least one of the inner layer and the outer layer of the bladder;
- the tube extending toward the open downstream end of the seam and through the opening positioned between the lateral sides of the seam in the bladder, the tube being adapted for connection to a fluid source for delivering fluid from the source to the hollow interior to inflate the bladder; and
- a seal extending between the lateral sides of the seam preventing fluid leakage between the tube and the opening in the bladder when the bladder is inflated.

10. A compression device as set forth in claim 9 wherein:
the bladder is a first bladder, the tube is a first tube, and the seal is a first seal; and
the compression device further comprises:
- a second bladder mounted on the sleeve having an inner layer positioned in use to face the patient's body, an outer layer opposite the inner layer positioned in use to face away from the patient's body, the inner layer and the outer layer being joined to form a hollow interior adapted for periodically receiving fluid to inflate the second bladder, the joined inner layer and outer layer being further joined by a seam having a sealed upstream end, an open downstream end, and sealed lateral sides extending between the upstream end and the downstream end, the second bladder including an opening positioned between the lateral sides of the seam and extending through at least one of the inner layer and the outer layer of the second bladder;
- a second tube extending toward the open downstream end of the seam and through the opening positioned between the lateral sides of the seam in the second bladder, the second tube being adapted for connection to a fluid source for delivering fluid from the source to the hollow interior to inflate the second bladder; and
- a second seal extending between the lateral sides of the seam preventing fluid leakage between the second tube and the opening in the second bladder when the second bladder is inflated.

11. A compression device as set forth in claim 10 further comprising:
- a third bladder mounted on the sleeve having an inner layer positioned in use to face the patient's body, an outer layer opposite the inner layer positioned in use to face away from the patient's body, the inner layer and the outer layer being joined to form a hollow interior adapted for periodically receiving fluid to inflate the third bladder, the joined inner layer and outer layer being further joined by a seam having a sealed upstream end, an open downstream end, and sealed lateral sides extending between the upstream end and the downstream end, the third bladder including an opening positioned between the lateral sides of the seam and extending through at least one of the inner layer and the outer layer of the third bladder;
- a third tube extending toward the open downstream end of the seam and through the opening positioned between the lateral sides of the seam in the third bladder, the third tube being adapted for connection to a fluid source for delivering fluid from the source to the hollow interior to inflate the third bladder; and
- a third seal extending between the lateral sides of the seam preventing fluid leakage between the third tube and the opening in the third bladder when the third bladder is inflated.

12. A compression device as set forth in claim 11 further comprising a fluid connector in fluid communication with said first tube, said second tube, and said third tube for connecting said first tube, said second tube, and said third tube to a fluid source to enable fluid delivery from the source to the hollow interior of the respective bladder.

13. A compression device as set forth in claim 11 wherein said first seam, said second seam, and said third seam include a U-shaped section.

14. A compression device as set forth in claim 11 wherein the opening in each of said first bladder, said second bladder, and said third bladder comprises a generally U-shaped portion.

15. A compression device as set forth in claim 11 wherein each of said first seal, said second seal, and said third seal comprises a weld extending between the lateral sides of the respective seam.

16. A compression device as set forth in claim 15 wherein each weld extends across the respective tube.

17. A compression device as set forth in claim 11 wherein the opening in each of said first bladder, said second bladder, and said third bladder extends through the outer layer of the respective bladder.

18. A compression device as set forth in claim 9 wherein:
the sleeve comprises an outer sheet and an inner sheet; and
the bladder is positioned between the outer sheet and the inner sheet.

* * * * *

UNITED STATES PATENT AND TRADEMARK OFFICE
CERTIFICATE OF CORRECTION

| | | |
|---|---|---|
| PATENT NO. | : 8,398,572 B2 | Page 1 of 1 |
| APPLICATION NO. | : 12/886864 | |
| DATED | : March 19, 2013 | |
| INVENTOR(S) | : Avitable | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this
Twenty-first Day of January, 2014

Michelle K. Lee
*Deputy Director of the United States Patent and Trademark Office*